(12) United States Patent
Yasuda et al.

(10) Patent No.: US 6,262,292 B1
(45) Date of Patent: Jul. 17, 2001

(54) METHOD FOR PRODUCING CYANOPHENYL DERIVATIVES

(75) Inventors: Hiroshi Yasuda; Kimitaka Ohshiro, both of Kanagawa; Kaneo Nozawa, Fukushima; Kohei Morikawa, Kanagawa, all of (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/343,268

(22) Filed: Jun. 30, 1999

Related U.S. Application Data

(60) Provisional application No. 60/091,309, filed on Jun. 30, 1998, provisional application No. 60/123,983, filed on Mar. 11, 1999, and provisional application No. 60/132,427, filed on May 4, 1999.

(30) Foreign Application Priority Data

| Oct. 19, 1998 | (JP) | 10-296330 |
| Nov. 11, 1998 | (JP) | 10-320787 |
| Dec. 15, 1998 | (JP) | 10-355582 |
| Mar. 29, 1999 | (JP) | 11-086058 |

(51) Int. Cl.$^7$ .................................................. C07C 255/00
(52) U.S. Cl. ............................................ 558/415; 558/416
(58) Field of Search ................................. 558/415, 416; 562/493, 863

(56) References Cited

FOREIGN PATENT DOCUMENTS

| 49-85041 | 8/1974 | (JP) . |
| 60-166655 | 8/1985 | (JP) ............................ C07C/121/76 |
| 64-47 | 1/1989 | (JP) ............................ C07C/63/06 |
| 1-31501 | 6/1989 | (JP) ............................ C07C/121/75 |

*Primary Examiner*—Joseph K. McKane
*Assistant Examiner*—Joseph Murray
(74) *Attorney, Agent, or Firm*—Sughrue, Mion, Zinn, Macpeak & Seas, PLLC

(57) ABSTRACT

The invention relates to (1) a process for producing a cyanobenzaldehyde compound by converting the aminomethyl group in a cyanobenzylamine compound into an aldehyde group using an oxidizing agent without impairing the cyano group, to (2) a process for producing a cyanobenzoyl halide compound by converting the aldehyde group in a cyanobenzaldehyde compound into an acid halide group without impairing the cyano group, and to (3) a process for producing a cyanobenzoic acid compound by reacting a cyanobenzaldehyde compound with a hypohalogenous compound.

According to the present invention, cyanophenyl derivatives that are useful as an intermediate of medical preparations, agricultural chemicals, liquid crystals, functional high molecular monomers and the like can be produced efficiently from raw materials that are obtained without difficulty.

27 Claims, No Drawings

METHOD FOR PRODUCING CYANOPHENYL DERIVATIVES

The present application claims a benefit of earlier filed U.S. applications Filing Nos. 60/091,309 (Filed Jun. 30, 1998), 60/123,983 (Filed Mar. 11, 1999) and 60/132,427 (Filed May 4, 1999).

FIELD OF THE INVENTION

The present invention relates to a process for the production of cyanophenyl derivatives. More particularly, the present invention relates to a process for the production of cyanobenzaldehyde compounds, cyanobenzoyl halide compounds and cyanobenzoic acid compounds from caynobenzylamine compounds as raw materials.

The cyanobenzaldehyde compounds, cyanobenzoyl halide compounds and cyanobenzoic acid compounds obtained by the present invention are important intermediates of medical preparations, agricultural chemicals, liquid crystals, functional high molecular monomers and the like.

BACKGROUND OF THE INVENTION

Several production processes have been conventionally known for the cyanobenzaldehyde compounds, cyanobenzoyl halide compounds and cyanobenzoic acid compounds.

First, a production process for p-cyano-benzaldehyde, a representative example of cyanobenzaldehyde compounds, will be described.

(1) The p-cyanobenzaldehyde is classically synthesized by converting p-cyanobenzoic acid into p-cyanobenzoyl chloride with a chlorinating agent such as thionyl chloride and subjecting the p-cyanobenzoyl chloride to Rosenmund reduction [see, Rapopport et al., J. Am. chem. Soc., 75 (1953), 1125].

(2) A method of reacting p-bromomethylbenzonitrile with hexamethylenetetramine in chloroform and subjecting the salt [ E]li precipitated to thermal decomposition with an acetic acid-water solvent is also known [see, Dyer et al., J. Chem. Soc., (1952) 4778].

(3) As a modification of (2), a method of reacting p-chloromethylbenzonitrile with hexamethylenetetramine in an oil-water two-layer system is known (see, JP-A-60-166655 (the term "JP-A" as used herein means an "unexamined published Japanese patent application)).

Further, (4) electrolytical oxidization methods of cyanobenzylamines such as a method of electrolytically oxidizing p-cyanobenzylamine in the presence of 2,6-lutidine and a perchlorate using 2,2,6,6-tetramethylplperidinyl-1-oxide as a mediator are also known [see, Semmelhack et al., J. Am. Chem. Soc., 105 (1983) 6732].

Furthermore, (5) a method of oxidizing p-cyano-N,N-dimethylbenzylamine with iodosylbenzene in the presence of a catalytic amount of iron-porphyrin complex (Smith et al., J. Chem. Soc. Chem. Commun., 64 (1985)).

These synthesis methods of p-cyanobenzaldehyde each has a problem.

In the Rosenmund reduction method in (1) above, this starting compound requires multiple stages for the synthesis thereof and is low in yield.

In the method of using p-halogenomethylbenzonitrile as a starting material in (2) and (3) above, p-tolunitrile as a raw material is difficult to procure and moreover, since hexamethylenetetramine in excess of the stoichiometric amount is required, a large amount of wastes is produced and this causes environmental problems.

Further, in the electrolytic oxidation of p-cyanobenzylamine in (4) above, an 8-fold amount of tertiary amine is necessary, a 20% molar amount of oxidation mediator is required and moreover, the oxidation mediator decomposes as the reaction proceeds, thus, this method is not suitable for the production in large quantities at a low cost.

Further, the oxidation of p-cyano-N,N-dimethylbenzylamine in (5) above, a stoichiometric amount of an oxidizing agent is used and a porphyrin complex catalyst which is expensive and tends to decompose is necessary, so that it is uneconomical.

As described in the foregoing, conventionally known techniques for producing p-cyanobenzaldehyde are disadvantageous in that the synthesis is cumbersome, a high-purity entity is difficult to obtain, and the raw material is not easily procured.

Furthermore, as the method of producing cyanobenzoyl halide compound, a method of reacting a corresponding cyanobenzoic acid compound with an acid halogenating agent has been proposed. As a representative example, a method of reacting p-cyanobenzoic acid with an acid chlorinating agent to obtain p-cyanobenzoyl chloride is recited.

There have been proposed (6) a method of using thionyl chloride as the acid chlorinating agent (JP-B-1-31501(the term "JP-B" as used herein means an "examined published Japanese patent application)), (7) a method of using oxalyl chloride (Robert J. Weikert, et al., J. Med. Chem., 3, 1630 (1991)) and (8) a method of using phosphorus pentachloride (Raffaello Fusco, et al., Ann. Chim (Rome), 42, 94 (1952)).

These methods have the following problems and hence they are not always advantageous for practice on an industrial scale.

That is, the method of using thionyl chloride in (6) above by-produces sulfur dioxide, which is a cause of air pollution and has the problem that separation and detoxification treatment of sulfur dioxide is costly.

The method of using oxalyl chloride in (7) above by-produces carbon monoxide, which is also a cause of air pollution and it has a problem that its detoxification treatment is costly.

Furthermore, the method of using phosphorus pentachloride in (8) above produces a by-product containing phosphorus compounds. Since it serves as a source of enrichment material for lakes and rivers and is a cause of environmental pollution, the phosphorus-containing byproduct has to be discarded after suitable treatment thereof.

As described above, the conventionally known production methods for cyanobenzoyl halide compounds have the problems that they involve a difficulty in separation and detoxification treatment of by-products and after the reaction, the treatment for reducing loads on environment upon disposal of by-products after the reaction is costly.

Further, several production methods for cyanobenzoic acid compounds are known. As a representative example, a production method for p-cyanobenzoic acid is cited.

p-Cyanobenzoic acid has classically been synthesized by (9) Sandmeyer reaction in which p-aminobenzoic acid is diazotized and reacted with copper cyanide (Lucas et al., J. Am. Chem. Soc., 51 (1929) 2718).

Furthermore, (10) a synthesis method of oxidizing tolunitrile with a strong oxidizing agent such as chromic acid or permanganic acid is also known (Levine et al., J. Org. Chem., 24, 115 (1959), Kattwinkel et al., Chem. Ber., 37, 3226 (1904)).

More recently, (11) it has been known that p-cyanobenzoic acid can be synthesized by carbonylating 4-chlorocyanobenzene using a palladium-phosphine catalyst in the presence of carbon monoxide (JP-A-64-47).

As related art to the present invention, (12) a method of oxidizing p-tolunitrile with sodium hypochlorite as an oxidizing agent using a ruthenium compound as an oxidizing catalyst in a two-layer system consisting of water and an organic solvent in the presence of a phase transfer catalyst (Yoel et al., J. Org. Chem., 51, 2880 (1986)). In the literature, tolunitrile has been reported to be converted to p-cyanobenzoic acid via p-cyanobenzaldehyde.

Furthermore, (13) as a method of oxidizing p-cyanobenzaldehyde, a method of using a cobalt catalyst in an oxygen atmosphere in the presence of acetic anhydride and n-butyraldehyde (Punniyamurthy et al., Tetrahedron Letters., 35, 2959 (1994)) and a method of using sodium perborate in acetic acid solvent (Norich et al., Tetrahedron, 45, 3299 (1989)) have been known.

However, these conventional production methods for cyanobenzoic acid have several problems.

The Sandmeyer method in (9) above needs dangerous copper cyanide and isolation and purification of p-cyanobenzoic acid is difficult under acidic conditions where hydrogen cyanide is released.

In the case where the oxidizing agent such as chromic acid or permanganic acid in (10) above is used, toxic heavy metal wastes are produced in excess of the stoichiometric amount so that a large amount of wastes containing toxic heavy metals is generated, which causes severe problems on the environment.

The carbonylation method in (11) above uses expensive palladium and phosphine so that it is uneconomical.

Furthermore, the method of using a ruthenium compound in (12) above needs 1 mol % of an expensive ruthenium compound and 5 mol % of a phase transfer catalyst as an indispensable component to a raw material so that it is an uneconomical method.

Furthermore, of the methods for the oxidization of p-cyanobenzaldehyde in (13) above, both the oxidation method with oxygen and the method using sodium perborate are low in yield.

As described above, there have been the problems that the cyanobenzoic acid compounds are difficult to obtain in pure forms since their synthesis is complexed according to the conventionally known production methods and raw materials are difficult to obtain.

SUMMARY OF THE INVENTION

Therefore, an object of the present invention is to provide a process for producing cyanobenzaldehyde compounds advantageously on an industrial scale using raw materials that are readily available and in fewer reaction steps.

Another object of the present invention is to provide a process for producing cyanobenzoyl halide compounds, which method imposes less load on the environment, is easy to detoxify the by-produced products, and produces cyanobenzoyl halide compounds in a high yield and a high purity on an industrial scale, using as raw materials cyanobenzaldehyde compounds that can be obtained efficiently by the process of the present invention.

Still another object of the present invention is to provide a process for producing cyanobenzoic acid compounds in a high yield and a high purity by an industrially advantageous method using as raw materials the cyanobenzaldehyde compounds that can be obtained by the process of the present invention efficiently.

DISCLOSURE OF THE INVENTION

The present inventors have found that an oxidation reaction starting from cyanobenzylamine compounds, which can be readily synthesized from phthalonitrile compounds and the like, using an oxidizing agent of the reagent, enables conversion of the aminomethyl group (—$CH_2NH_2$) into an aldehyde group (—CHO) without impairing the cyano group on the benzene ring to obtain cyanobenzaldehyde compounds.

Furthermore, the present inventors have found a production method for a cyanobenzoyl halide compound that has hitherto been quite unknown and starts from a cyanobenzaldehyde compound and can convert the aldehyde group (—CHO) to an acid halide group (—COY: Y represents a chlorine atom or a bromine atom) without impairing the cyano group on the benzene ring.

Moreover, the present inventors have found that reaction of the cyanobenzaldehyde compounds as starting materials and a hypohalogenous compound in water or a mixed solvent of water and an aprotic polar solvent affords cyanobenzoic acid compounds in a high purity and in a high yield.

Based on these findings, the present invention provides the following methods for the production of cyanobenzaldehyde compounds, cyanobenzoyl halide compounds, and cyanobenzoic compounds.

1) A process for producing a cyanobenzaldehyde compound comprising reacting a cyanobenzylamine compound with an oxidizing agent.

2) The process for producing a cyanobenzaldehyde compound as described in 1) above, wherein a cyanobenzylamine compound obtained by reducing a phthalonitrile compound with hydrogen is reacted with the oxidizing agent.

3) The process for producing a cyanobenzaldehyde compound as described in 1) above, wherein the reaction with the oxidizing agent is performed in the presence of a transition metal compound.

4) The process for producing a cyanobenzaldehyde compound as described in 3) above, wherein the reaction with the oxidizing agent is performed in the presence of a transition metal compound with an oxidizing agent (excluding the transition metal compound).

5) The process for producing a cyanobenzaldehyde compound as described in 4) above, wherein the oxidizing agent is air.

6) The process for producing a cyanobenzaldehyde compound as described in 1) above, wherein the reaction with the oxidizing agent is performed in the presence of ammonia and formaldehyde or its condensate and water under acidic conditions.

7) The process for producing a cyanobenzaldehyde compound as described in 1) above, wherein the reaction with the oxidizing agent is performed in a mixed solvent of water and an organic solvent.

8) The process for producing a cyanobenzaldehyde compound as described in 1) above, wherein the reaction with the oxidizing agent is performed in a solvent at a pH in the range of from 1.5 to 6.5.

9) The process for producing a cyanobenzaldehyde compound as described in 6) above, wherein the condensate between ammonia and formaldehyde is hexamethylenetetramine.

10) The process for producing a cyanobenzaldehyde compound as described in 1) above, wherein the oxidizing agent is a persulfate salt and the reaction is performed in an aqueous solution.

11) The process for producing a cyanobenzaldehyde compound as described in 10) above, wherein the reaction with the oxidizing agent is performed in an aqueous solution further containing an organic solvent.

12) The process for producing a cyanobenzaldehyde compound as described in 1) above, wherein the reaction with the oxidizing agent is performed by reacting a cyanobenzylamine compound with a halogenating agent, and then with a basic compound, and further treating the reaction product with an acidic aqueous solution.

13) The process for producing a cyanobenzaldehyde compound as described in 12) above, wherein the reaction with the oxidizing agent is performed in the presence of a radical initiator.

14) The process for producing a cyanobenzaldehyde compound as described in 1) above, wherein the cyanobenzylamine compound is a compound represented by the following general formula (I):

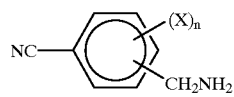

(I)

(wherein —CH$_2$NH$_2$ and —X represent substituents on the benzene ring, —CH$_2$NH$_2$ is present at the meta- or para-position of the cyano group, and X represents a chlorine atom or a fluorine atom, and n is 0 or an integer of 1 to 4, provided that when n is 2 or greater, X groups may be the same or different) and the cyanobenzaldehyde compound is a compound represented by the following general formula (II)

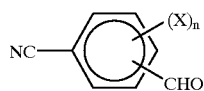

(II)

(wherein —CHO and —X represent substituents on the benzene ring, —CHO is present at the meta- or para-position of the cyano group, X represents a chlorine atom or a fluorine atom, n represents 0 or an integer of from 1 to 4, provided that when n is 2 or greater, the X groups may be the same or different).

15) The process for producing a cyanobenzaldehyde compound as described in 14) above, wherein the cyanobenzylamine compound is p- or m-cyanobenzylamine and the cyanobenzaldehyde compound is p- or m-cyanobenzaldehyde correspondingly.

16) A process for producing a cyanobenzoyl halide compound, wherein after the cyanobenzylamine compound is reacted with the oxidizing agent to form a cyanobenzaldehyde compound, the aldehyde group is converted into an acid halide group without impairing the cyano group on the benzene ring of the cyanobenzaldehyde compound.

17) A process for producing a cyanobenzoyl halide compound, comprising converting an aldehyde group into an acid halide group without impairing the cyano group on the benzene ring of the cyanobenzaldehyde compound.

18) The process for producing a cyanobenzoyl halide compound as described in 17) above, wherein the aldehyde group is converted into the acid halide group with a halogenating agent.

19) The process for producing a cyanobenzoyl halide compound as described in 18) above, wherein the reaction is performed in the presence of a radical initiator.

20) The process for producing a cyanobenzoyl halide compound as described in 18) above, wherein the halogenating agent is chlorine and the acid halide group is an acid chloride.

21) The process for producing a cyanobenzoyl halide compound as described in 17) above, wherein the conversion reaction of the aldehyde group in the cyanobenzaldehyde compound into the acid halide group is performed in a molten state by mixing the cyanobenzaldehyde with the cyanobenzoyl halide compound.

22) The process for producing a cyanobenzoyl halide compound as described in 17) above, wherein the cyanobenzaldehyde compound is a compound represented by the following general formula (II)

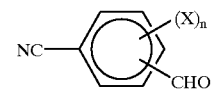

(II)

(wherein —CHO and —X represent substituents on the benzene ring, —CHO is present at the meta- or para-position of the cyano group, X represents a chlorine atom or a fluorine atom, n represents 0 or an integer of from 1 to 4, provided that when n is 2 or greater, the X groups may be the same or different) and the cyanobenzoyl halide compound is a compound represented by the following general formula (IV)

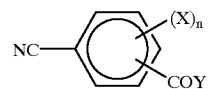

(IV)

(wherein —COY and —X represent substituents on the benzene ring, —COY is present at the meta- or para-position of the —CN, X represents a chlorine atom or a fluorine atom, and n represents 0 or an integer of from 1 to 4 and Y represents a chlorine atom or a fluorine atom, provided that when n is 2 or greater, the X groups may be the same or different).

23) The process for producing a cyanobenzoyl halide compound as described in 22) above, wherein the cyanobenzaldehyde represented by the general formula (II) is m-cyanobenzaldehyde or p-cyanobenzaldehyde and the cyanobenzoyl halide compound represented by the general formula (IV) is m-cyanobenzoyl chloride or p-cyanobenzoyl chloride correspondingly.

24) A process for producing a cyanobenzoic acid compound, comprising reacting a cyanobenzylamine compound with an oxidizing agent to form a cyanobenzaldehyde compound and then oxidizing the aldehyde group without impairing the cyano group on the benzene ring of the cyanobenzaldehyde compound.

25) A process for producing a cyanobenzoic acid compound represented by the general formula (V)

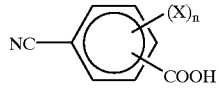

(V)

(wherein —COOH and —X represent substituents on the benzene ring, —COOH is present at the meta- or para-position of the —CN, X represents a chlorine atom or a fluorine atom, n represents 0 or an integer of from 1 to 4, provided that when n is 2 or greater, the X groups may be the same or different), comprising reacting a cyanobenzaldehyde compound represented by the general formula (II)

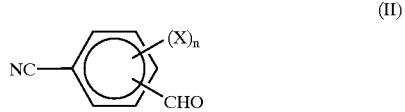

(wherein —CHO and —X represent substituents on the benzene ring, —CHO is present at the meta- or para-position of the —CN, X represents a chlorine atom or a fluorine atom, n represents 0 or an integer of from 1 to 4, provided that when n is 2 or greater, the X groups may be the same or different) with a hypohalogenous acid compound.

26) The process for producing a cyanobenzoic acid compound as described in 25) above, wherein the reaction of the cyanobenzaldehyde compound with the hypohalogenous compound is performed in an aqueous solution in the presence of aprotic polar solvent.

27) The process for producing a cyanobenzoic acid compound as described in 25) above, wherein the reaction of the cyanobenzaldehyde compound with the hypohalogenous compound is performed in an aqueous solution at a pH in the range of from 5 to 10.

28) The process for producing a cyanobenzoic acid compound as described in 25) above, wherein the cyanobenzaldehyde represented by the general formula (II) is m-cyanobenzaldehyde or p-cyanobenzaldehyde and the cyanobenzoic acid compound represented by the general formula (V) is m-cyanobenzoic acid or p-cyanobenzoic acid correspondingly.

DETAILED DESCRIPTION OF THE INVENTION (a) Production Method for a Cyanobenzaldehyde Compound
Cyanobenzylamine Compound In the process of the present invention, examples of the unsubstituted cyanobenzylamine compound used as a raw material include p-cyanobenzylamine, m-cyanobenzylamine, etc. These can be readily synthesized by reducing one of two nitrile groups of terephthalonitrile and isophthalonitrile, respectively (JP-A-49-85041).

Next, explanation will be made of substituted forms. Substituents are not limited particularly any substituent may be used so long as it is inert to the reaction of the present invention. Examples thereof include a halogen atom, an alkyl group (preferably $C_1$ to $C_5$), an alkoxy group (preferably $C_1$ to $C_5$), etc. Among them, halogen substituted cyanobenzylamine compounds will be explained as a preferred example. For example, chlorinated cyanobenzylamine compounds such as 4-cyano-2,3,5,6-tetrachlorobenzylamine, or 3-cyano-2,4,5,6-tetrachlorobenzylamine can be readily synthesized by reducing one of two nitrile groups of chlorinated terephthalonitrile compounds such as tetrachloroterephthalonitrile or chlorinated isophthalonitrile compounds such as tetrachloroisophthalonitrile obtained by chlorination of terephthalonitrile or isophthalonitrile.

Fluorinated cyanobenzylamine compounds such as 4-cyano-2,3,5,6-tetrafluorobenzylamine or 3-cyano-2,4,5,6-tetrafluorobenzylamine can be readily synthesized by reducing one of two nitrile groups of fluorinated terephthalonitrile compounds such as tetrafluoroterephthalonitrile or fluorinated isophthalonitrile compound such as tetrafluoroisophthalonitrile obtained by fluorination reaction of chlorinated terephthalonitrile compounds such as tetrachloroterephthalonitrile or chlorinated isophthalonitrile compounds such as tetrachloroisophthalonitrile.

In the production method for cyanobenzaldehyde compounds according to the present invention, the synthesis reaction of cyanobenzaldehyde compounds used is a reaction of oxidizing the aminomethyl group of the cyanobenzylamine compounds with a reagent of an oxidizing agent instead of using a direct or indirect electrochemical oxidation reaction.

The oxidizing agent used in the present invention may be any organic or inorganic compound that converts an aminomethyl group into an aldehyde group directly or indirectly.

Specific examples thereof include (i) a process for using a transition metal compound, (ii) a process for using ammonia and formaldehyde or a condensate thereof, (iii) a process for using a persulfate salt, and (iv) a process for reacting with a halogenating agent, and then reacting with a basic compound and hydrolyzing in an acidic aqueous solution.

(i) A Process for Using a Transition Metal Compound

It is possible to directly synthesize a cyanobenzaldehyde compound from a cyanobenzylamine compound using an oxide of a transition metal such as chromium, manganese, iron, and ruthenium, in a high oxidation state.

However, in addition to a desired cyanobenzaldehyde compound, cyanobenzoic acid compounds that are in a further oxidized state, cyanobenzamide compounds and phthalonitrile compounds are by-produced, and cyanobenzylamine dimer obtained by deamination dimerization of a cyanobenzylamine compound are also by-produced, so that the selectivity of cyanobenzaldehyde compound will not be increased.

Of these compounds, the cyanobenzylamine dimer can be derived to a cyanobenzaldehyde compound. That is, cyanobenzylamine dimer is hydrolyzed to recover a cyanobenzylamine compound, which is reused as a raw material, to obtain a cyanobenzylaldehyde compound.

Furthermore, there is a process for deriving a cyanobenzylamine compound into a cyanobenzaldehyde compound in which the cyanobenzylamine compound is derived into the cyanobenzaldehyde compound not directly but after deriving into a suitable intermediate that can be selectively derived into the cyanobenzaldehyde compound.

For example, a cyanobenzylamine compound represented by the general formula (I) is dehydrogenated with a transition metal compound to be derived into a corresponding imine compound represented by the general formula (III), and the imine is hydrolyzed to synthesize a cyanobenzaldehyde compound represented by the general formula (II) (cf. Reaction Scheme (1)).

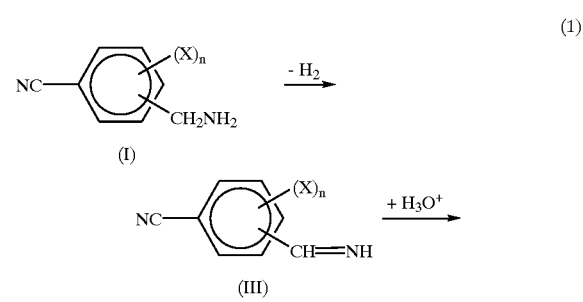

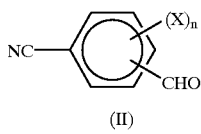

(II)

Note that the compound obtained by dehydrogenation reaction of the cyanobenzylamine compound may be any compound so long as it is in the same oxidation state as the aldehyde compound, such as acetalated compounds or hydroxylamine compounds except for the imine compounds. These synthesis intermediates may be isolated and hydrolyzed or may be hydrolyzed as they are in the same reaction system when they cannot be isolated.

The transition metal compounds that are suitable for the reaction include a copper compound, a palladium compound, a ruthenium compound, a cobalt compound, a chromium compound, a manganese compound, an iron compound, a tungsten compound, a molybdenum compound, etc.

These transition metal compounds may be in high oxidation state and used singly in the same amount as or in excess of the stoichiometric amount with respect to the cyanobenzylamine compound but the reaction can proceed in a catalytic amount below the stoichiometric amount by co-existence of one or more other oxidizing agents such as oxygen (air) and peroxides. In particular, combined use of a transition metal and air is preferred.

In addition to the transition metal compound, there are various compounds that can be used as an oxidizing agent. Among the methods using them, for the oxidation reaction of cyanobenzylamine compounds of the present invention, are particularly preferred (ii) a process for using ammonia and formaldehyde or a condensate thereof, (iii) a process for using a persulfate salt, and (iv) a process for reacting with a halogenating agent, and then reacting with a basic compound and hydrolyzing in an acidic aqueous solution.

Hereafter, representative methods for converting cyanobenzylamine compounds into cyanobenzaldehyde compounds with an oxidizing agent will be explained.

(ii) A Process for Using Ammonia and Formaldehyde

First, the case where ammonia and formaldehyde or a condensate thereof are used as an oxidizing agent will be explained in detail hereinbelow.

The reaction in the present invention is performed by charging a cyanobenzylamine compound, ammonia and formaldehyde or a condensate of ammonia and formaldehyde (such as hexamethylenetetramine) into a reaction vessel in the presence of water under an acidic condition, elevating the temperature of the mixed solution to the reaction temperature while stirring, and heating and stirring the solution for a predetermined time.

The reaction starting materials may be charged and reacted in an atmospheric pressure. The reaction vessel is suitably a glass vessel or an acid-proof metal vessel.

Although details of the reaction mechanism is unknown, the reaction is presumed to proceed by the following mechanism from experimental data and a known publication (Organic Reaction, 8 (1954), 197).

As elementary reaction process, oxidation-reduction reaction takes place between an imine compound resulting from dehydration and condensation of formaldehyde and ammonia (formula (2)) and p-cyanobenzylamine to produce methylamine and p-cyanobenzylimine (formula (3)). The p-cyanobenzylimine is hydrolyzed by an acidic water solvent to produce p-cyanobenzaldehyde (formula (4)). The net reaction summing the elementary reaction processes (2), (3) and (4), is represented by formula (5).

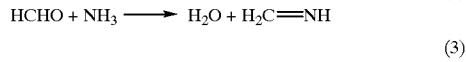

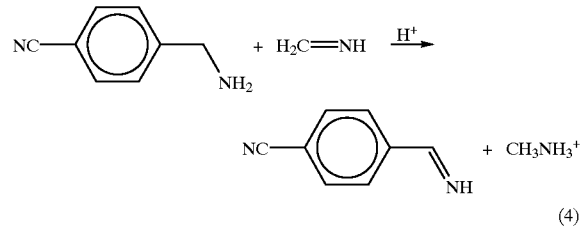

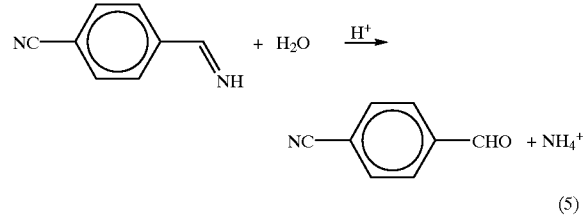

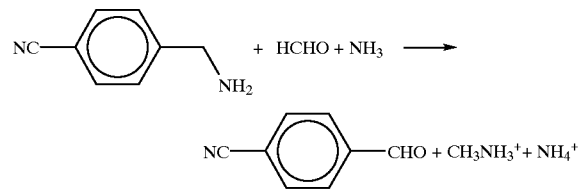

A typical dehydration and condensation compound of ammonia and formaldehyde is hexamethylenetetramine (formula (6)).

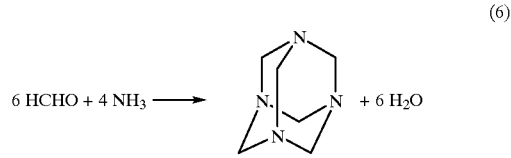

For explaining the mechanism of producing hexamethylenetetramine, the following theory may be considered

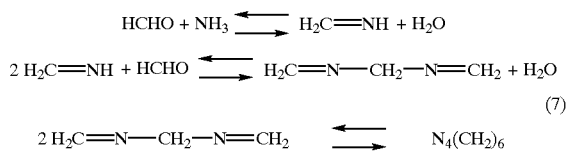

[see, Bose, J. Ind. Chem. Soc. 34 (1957), 663] (Formula 7). In formula (7), the molecular formula $N_4(CH_2)_6$ is hexamethylenetetramine.

The ammonia may be either an ammonia molecule itself or a compound capable of liberating ammonia under the reaction conditions. Also, the formaldehyde may be either a formaldehyde molecule itself or a compound capable of liberating formaldehyde under the reaction conditions.

The reaction in the present invention requires the presence of ammonia and formaldehyde or of a condensate of ammonia and formaldehyde. The ammonia which can be used includes ammonia as a gas and aqueous ammonia as an aqueous solution. Also, an organic or inorganic salt capable of liberating ammonia under the reaction conditions, such as ammonium acetate and ammonium carbonate, may be used.

The formaldehyde which can be used includes formaldehyde as a gas, formalin as an aqueous solution, a dehydration condensate capable of liberating formaldehyde under the reaction conditions, and an acetal of formaldehyde such as formaldehyde dimethyl acetal.

The amount of the ammonia used in the present invention is preferably from 1 to 8 as a molar ratio to the cyanobenzylamine compound.

The amount of formaldehyde used in the present invention is preferably from 1 to 12 as a molar ratio to the cyanobenzylamine compound.

If the amount of ammonia or formaldehyde to the amount of the cyanobenzylamine compound is too small, the reaction takes a long time to complete, whereas if it is excessively large, a large amount of organic or inorganic compounds are by-produced as a result of the reaction.

In the case of using a condensate of ammonia and formaldehyde, the molar ratio thereof to the cyanobenzylamine compound is preferably from 1 to 12 for the condensate where formaldehyde is 1 mol.

In the case of hexamethylenetetramine which can be suitably used in the present invention, the molar ratio thereof to the cyanobenzylamine compound is preferably from 0.5 to 2, more preferably from 0.7 to 1.3. If the amount of hexamethylenetetramine to the amount of the cyanobenzylamine compound is too small, the reaction takes a long time to complete, whereas if it is too large, removal of the organic or inorganic by-product compounds generated as a result of the reaction is laborsome.

In this reaction, use of water is indispensable. The water may be used in an amount employed for use as a solvent or in a trace amount. Water may be added either by adding the total amount upon charging of raw materials or portionwise in accordance with the progress of the reaction.

The reaction is performed in an acidic condition. The acid used is an organic or inorganic protonic acid.

The inorganic acid is preferably a sulfuric acid, a nitric acid, a hydrochloric acid or a phosphoric acid.

The organic acid which can be used includes a carboxylic acid such as acetic acid and butyric acid, and a sulfonic acid such as tosylic acid. A low boiling point carboxylic acid which can concomitantly serve as a solvent is particularly preferred. Also, a Lewis acid capable of reacting with a protonic solvent to liberate a protonic acid, such as aluminum chloride and stannic chloride, may be used. Acids may be added either by adding the total amount upon charging of raw materials or portionwise in accordance with the progress of the reaction.

In the reaction, the pH range is important. The cyanobenzaldehyde compound is generally produced when the reaction mixture is in weakly acidic condition. If the reaction mixture is in strongly acidic condition (pH<1), the yield of the cyanobenzaldehyde compound extremely decreases, and if it is in alkaline condition (pH>8), a desired reaction does not usually take place and almost no cyanobenzaldehyde compound can be obtained. The reaction is preferably performed under the condition of pH=1.5 to 6.5.

When the reaction is performed using an acidic aqueous solution containing water alone as a medium, a reaction starting material, an intermediate or a product may sometimes precipitate. In order to prevent precipitation of a starting material, a product or the like, an organic solvent may be mixed. Examples of the organic solvent which can be used include hydrocarbon-based solvents such as toluene and xylene, alcohol-based solvents such as methanol and ethanol, carboxylic acid-based solvents such as acetic acid and propionic acid, halogen-based solvents such as chloroform and 1,2-dichloroethane, nitrile-based solvents such as acetonitrile and propionitrile, and ether-based solvents such as dioxane and 1,2-dimethoxyethane.

The reaction may be performed after preparing a homogeneous solution by adding acetic acid or ethanol, or may be performed in a two-layer system using toluene or 1,2-dichloroethane. The solvent may be selected according to the purification method.

The amount of solvent in the reaction is suitably from 3 to 10 times, preferably from 4 to 6 times, to the total weight of the cyanobenzylamine compound, ammonia and formaldehyde or of the cyanobenzylaminJe compound and a condensate of ammonia and formaldehyde (e.g., hexamethylenetetramine).

The reaction temperature is preferably from 50 to 150° C., more preferably from 70 to 130° C., because if the reaction temperature is excessively low, the reaction proceeds at a low speed, whereas if it is too high, the cyanobenzaldehyde compound produced is decomposed to cause reduction in the yield.

The reaction time varies depending on the reaction temperature or the composition of solvent, however, it is preferably from 30 minutes to 10 hours.

The process for purifying the cyanobenzaldehyde compound obtained by the reaction in the present invention will be explained taking p- or m-cyanobenzaldehyde as an example.

In the reaction in the present invention, sometimes colored p- or m-cyanobenzaldehyde is obtained depending on the reaction conditions, for example, as a result of too much heating or too long a reaction time.

There are various coloring components. In the case of formaldehyde or ammonia derived colored products, the coloring components are adhered on the surface of p- or m-cyanobenzaldehyde and can be removed by treating with an acidic aqueous solution. For this purpose, an aqueous sulfuric acid solution of 10% or less is preferable. By heating p- or m-cyanobenzaldehyde together with an aqueous sulfuric acid solution to heat-melting the p- or m-cyanobenzaldehyde with vigorous stirring, and then cooling the reaction mixture with vigorous stirring, scaly p- or m-cyanobenzaldehyde can be obtained. Alternatively, p- or m-cyanobenzaldehyde may be extracted with hot water without heat-melting it. Furthermore, when high boiling substances, etc. are contained, distilling off p- or m-cyanobenzaldehyde together with water (no azeotropy takes place since the boiling point is 100° C. or more) gives rise to pure p- or m-cyanobenzaldehyde. In the case of p-cyanobenzaldehyde, it is distilled off together with water at a boiling point of from 100.5 to 105° C. (atmospheric pressure), and is obtained in an amount of from about 0.5 to 3 g per 100 g water. The cyanobenzaldehyde compounds may be purified by other methods such as distillation or recrystallization.

(iii) A Process for Using Persulfate Salts

Next, explanation will be made of the case where persulfate salts are used.

The reaction in the present invention is performed by charging preferably a cyanobenzylamine compound, a persulfuric acid salt and water in a reaction vessel and heating at a predetermined reaction temperature for a predetermined time with stirring.

The reaction starting materials may be charged and reacted in an atmospheric pressure. The reaction vessel is suitably a glass vessel or an acid-proof metal vessel.

Although the reaction mechanism of oxidizing the aminomethyl group of benzylamine with a persulfate salt has not been completely elucidated yet, thus far a dimer of benzylamine has been formed but substantially no benzaldehyde has been obtained.

On the contrary, in the case of the cyanobenzylamine compound having a cyano group at the p- or m-position thereof used in the present invention, dimers of the cyanobenzylamine compound is difficult to form or if formed it tends to be decomposed readily to form a cyanobenzaldehyde compound which is the object compound and the cyanobenzylamine compound, which is the starting material. Also, in the case of the cyanobenzaldehyde compound as the product, unlike the aldehyde group of the benzaldehyde having no cyano group being oxidized readily with a persulfate salt, the aldehyde group of the cyanobenzaldehyde compound is relatively stable to persulfate salts, so that persulfate salts are considered to oxidize aminomethyl groups preferentially than aldehyde groups.

Although the details of the reaction mechanism is unknown, it is presumed from experimental data that the reaction proceeds by the following mechanism.

Explanation will be made taking as an example the reaction of p-cyanobenzylamine to p-cyanobenzaldehyde by oxidation with sodium persulfate.

A cyanobenzylamine compound is dehydrogenated with sodium persulfate to form a corresponding imine. The imine will dimerize or react with unused p-cyanobenzylamine to form a dimer of imine depending on the reaction mixture (neutral to basic).

That is, as described in reference examples which follow, addition of a base such as sodium bicarbonate to the reaction system of sodium persulfate and p-cyanobenzylamine to maintain the reaction mixture at neutral to basic gives rise to a dimer of p-cyanobenzylamine (deammoniation dimerization of mine) selectively but no p-cyanobenzaldehyde is obtained.

However, in the present invention, sodium persulfate is converted to sodium hydrogen sulfate as a result of dehydrogenation reaction of p-cyanobenzylamine and the reaction system becomes acidic. Under acidic conditions, the dimers of imine and p-cyanobenzylamine compound, respectively, are hydrolyzed to form p-cyanobenzaldehyde.

In the reaction, the persulfate salt that can be used includes ammonium persulfate, sodium persulfate, potassium persulfate, etc.

In the reaction system in the present invention, according as the persulfate salt is consumed, the reaction system becomes increasingly acidic. In acidic range, the persulfate salt will be gradually decomposed so that use of a slightly excess amount of persulfate salt with respect to the cyanobenzylamine compound may be effective in order to complete the reaction. The amount of persulfate salt is preferably 1 to 1.8 mol. more preferably 1.1 to 1.3, per mol of cyanobenzylamine compound.

In the reaction in the present invention, a transition metal compound may be used as a catalyst. The transition metal compound is effective in activation of the persulfate salt, allowing the reaction to proceed in a milder condition at low temperatures than in the absence of transition metal catalysts. There can be used transition metal compounds that cause a single electron oxidation-reduction reaction, for example, a silver compound, a copper compound, an iron compound, a cerium compound, a manganese compound, a titanium compound, etc. Furthermore, use of transition metal ion compounds having a suitable oxidation number, for example, a monovalent silver compound such as silver nitrate, a monovalent copper compound such as copper chloride, a divalent iron compound such as ferrous sulfate, a trivalent cerium compound such as cerium trichloride, a divalent manganese compound such as manganese (II) acetate, a trivalent titanium compound such as titanium trichloride, etc., can eliminate an induction period for the activation to shorten the reaction time. The transition metal compound is used in a proportion of 0.0001 to 0.01 mol per mol of persulfate salt.

The reaction in the present invention has to be performed in an aqueous solution. When water is used alone for the reaction, a reaction starting material, an intermediate or a product may sometimes precipitate. In order to prevent precipitation of a starting material or a product, an organic solvent may be mixed.

Examples of the organic solvent which can be used include hydrocarbon-based solvents such as toluene and xylene, alcohol-based solvents such as methanol and ethanol, halogen-based solvents such as chloroform and 1,2-dichloroethane, nitrile-based solvents such as acetonitrile and propionitrile, and ether-based solvents such as dioxane and 1,2-dimethoxyethane.

The reaction may be performed after preparing a homogeneous solution by adding acetonitrile or ethanol, or may be performed in a two-layer system using toluene or 1,2-dichloroethane. The solvent may be selected according to the purification method.

The amount of solvent in the reaction is suitably from 3 to 30 times, preferably from 5 to 10 times, to the weight of the cyanobenzylamine compound.

The reaction temperature is preferably from 20 to 110° C., more preferably from 40 to 80° C., because if the reaction temperature is excessively low, the reaction proceeds at a low speed, whereas if it is too high, the cyanobenzaldehyde compound produced is decomposed to cause reduction in the yield. When a transition metal compound is added, the reaction may be performed from 0 to 80° C., preferably 20 to 70° C.

The reaction time varies depending on the starting material, reaction temperature or the composition of solvent, however, it is preferably from 20 minutes to 10 hours.

(iv) A Process for Using a Halogenating Agent, a Basic Compound and an Acidic Aqueous Solution Next, explanation will be made of a process for reacting a cyanobenzylamine compound with a halogenating agent and then with a basic compound and hydrolyzing the reaction product in an acidic aqueous solution.

The reaction in the present invention is performed by charging preferably a cyanobenzylamine compound and a halogenating agent in a reaction vessel and elevating the temperature to a reaction temperature with stirring and heating and stirring for a predetermined time for reaction and after the disappearance of the cyanobenzylamine compound, charging a basic compound in the reaction vessel, performing dehalogenation reaction and then rendering the solution acidic in the presence of water.

The charging of raw materials and performance of reaction are not limited particularly and may be performed usually under atmospheric pressure. The reaction vessel is suitably a glass vessel or an acid-proof metal vessel.

The "halogenating agent" as used in the reaction refers to a compound that can introduce a halogen atom in the amino group of the cyanobenzylamine compound.

The "base" was used in the reaction refers to a compound that has an capability of trapping a protic acid by acid-base reaction.

The presumptive reaction route that is considered to be involved in the reaction in the present invention will be explained taking as a representative example the reaction of from p-cyanobenzylamine to p-cyanobenzaldehyde.

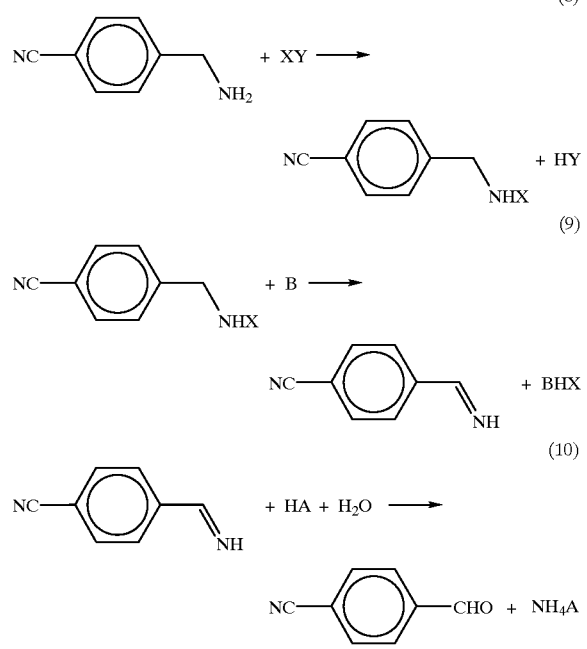

p-Cyanobenzylamine and a halogenating agent (XY) are reacted and a primary amino group is halogenated (formula (8), hereafter, this reaction is referred to as "halogenation").

Reaction of a base (B) with p-cyanobenzylamine with the amino group being halogenated causes a dehydrohalogenation reaction to take place to form an imine (formula (9), hereafter, this reaction is referred to as "dehydrohalogenation").

Then, hydrolysis of the imine in the presence of an acid (HA) results in the formation of p-cyanobenzaldehyde (formula (10), hereafter, this reaction is referred to as "acid hydrolysis").

In the halogenation reaction, the base is added preferably after the reaction of p-cyanobenzylamine with the halogenating agent is completed. Although the base may be added in the presence of the halogenating agent to shorten the process, a dehydrohalogenation reaction takes place in the same reaction system to form an imine. The imine reacts with unused p-cyanobenzylamine to by-produce a dimer of p-cyanobenzylamine, resulting in that sometimes the yield of p-cyanobenzaldehyde is decreased.

In the case where a volatile halogenating agent is used upon the halogenation, the halogenating agent can be removed by introduction of nitrogen after the reaction. However, the non-volatile halogenating agent may be removed by decomposition with a suitable reducing agent or the like.

Acid hydrolysis is performed after completion of the dehydrohalogenation to form an aldehyde.

Furthermore, the presence of an excess of halogenating agent upon the halogenation represented by the formula (8) or low selectivity of a monohalogen form sometimes gives rise to an N-dihalogen form of cyanobenzylamine compound (formula (11)).

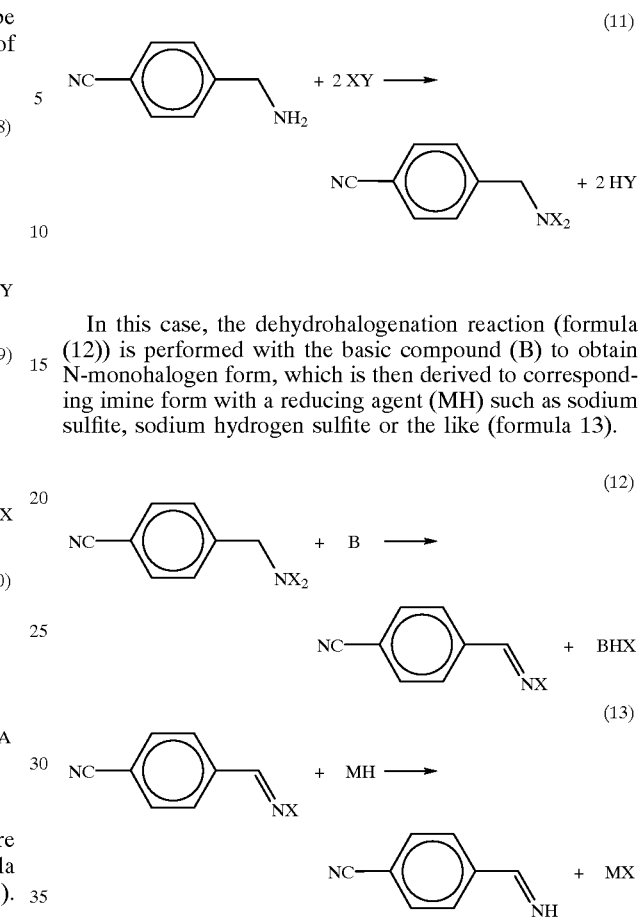

In this case, the dehydrohalogenation reaction (formula (12)) is performed with the basic compound (B) to obtain N-monohalogen form, which is then derived to corresponding imine form with a reducing agent (MH) such as sodium sulfite, sodium hydrogen sulfite or the like (formula 13).

Thereafter, the reaction may be performed in the same manner as in formula (10). In this case, an N-monohalogen form may be hydrolyzed directly without using any reducing agent. However, this is not preferred since N-monohalogen form is said to be equivalent to an oxime equivalent and its hydrolysis needs relatively stringent conditions so that there is the fear that the cyano group could be decomposed. Furthermore, due to the presence of an excess of base in the formula (8), there is sometimes the case that the resultant halogenoimine will be further undergone dehydrohalogenation reaction to form a nitrile. Thus, when N-dihalogenation takes place, there will appear a route where excess reduction operation and by-products will be generated, so that it is preferred to stop the reaction upon halogenation when N-monohalogen forms are obtained.

The halogenating agent to be used in the reaction in the present invention is not limited particularly and those halogenating agents used in organic synthesis in general.

For example, there may be used halogen molecules such as chlorine, bromine and iodine, mixed halogen molecules such as bromine chloride (BrCl) and iodine bromide (IBr), haloimides or haloamides such as N-chlorosuccinimide, N-bromosuccinimide, and N-bromoacetoamide, hypohalogenous acids such as hypochlorous acid and hypobromous acid, hypohalogenous acid salts or hypohalogenous acid esters such as calcium hypochlorite ($Ca(ClO)_2$) and t-butyl hypochlorite, chlorides or bromides such as sulfuryl chloride and sulfuryl bromide.

The amount of halogenating agent to be used is optimally 1 mol per mol of the cyanobenzylamine compound and its use around such a usage is preferred. Furthermore, the reaction temperature is in the order of 20 to 120° C., preferably 40 to 80° C. The reaction time is preferably from 0.5 to 8 hours.

In the reaction between the cyanobenzylamine compound and the halogenating agent, the reaction is effectively promoted by the presence of a radical initiator.

The radical initiator includes azobis compounds such as azobisisobutyronitrile, diacyl peroxides such as benzoyl peroxide, dialkyl peroxides such as di-t-butyl peroxide and dicumyl peroxide, hydroperoxides such as t-butyl hydroperoxide and cumene hydroperoxide, alkyl peresters such as t-butyl peracetate and t-butyl perbenzoate, etc.

In the reaction in the present invention, the radical derived from halogen is released to promote the reaction according as the reaction proceeds, so that the amount of radical initiator to be added initially may be extremely small.

The solvent for reaction between the base and the compound obtained by the reaction of the cyanobenzylamine compound with the halogenating agent may be the same as the solvent for the reaction of the cyanobenzylamine compound with the halogenating agent or a mixed solvent obtained by addition of a different solvent, or the solvent may be replaced. The reaction temperature is on the order of 0 to 80° C., preferably 10 to 50° C. If the reaction temperature is lower than 0° C., it takes a very long time for the reaction to be completed and if the reaction temperature is higher than 80° C., the substrate for the reaction could be decomposed to decrease the yield of reaction. The reaction time is preferably 30 minutes to 10 hours. The reaction time may vary depending on the amount of a base to be added and on the reaction temperature. The base is necessary in an at least equimolar amount with respect to the charged cyanobenzylamine compound. In the case where the solution is of a two-layer system or a weak base is used, use of an excess of base will increase the rate of dehydrohalogenation reaction.

Furthermore, in the case where an acidic compound is produced by the halogenation reaction in the preceding step, addition of a base in an amount sufficient to trap an excess acid as a salt is necessary.

The base which can be used in the present invention is an organic or inorganic basic compound.

As the organic basic compound can be used amines, nitrogen-containing heterocyclic compounds, etc., preferably tertiary amines, nitrogen-containing heterocyclic compounds. For example, pyridine, triethylamine, N-methylmorpholine, etc. are preferred.

The inorganic basic compound which can be used includes alkali and alkaline earth metal hydroxides such as sodium hydroxide, potassium hydroxide and magnesium hydroxide, alkaline earth metal oxides such as magnesium oxide and calcium oxide, alkali metal peroxides such as sodium peroxide and potassium peroxide, alkali metal hyper oxides such as sodium hyper oxide and potassium hyper oxide, alkali metal carbonates such as sodium hydrogen carbonate, potassium hydrogen carbonate, sodium carbonate, and potassium carbonate, alkali metal alkoxides such as sodium methoxide, sodium ethoxide and potassium tertiary butyl oxide, etc.

The acid hydrolysis, the final step, will be explained below.

The acid hydrolysis reaction is performed preferably in an acidic solution containing water at a pH of from 1 to 6, preferably at a pH of from 3 to 5.

The amount of acid is equimolar or more with respect to the imine produced in the dehydrohalogenation reaction and in the case where an excess of base is to be trapped as a salt, addition of an acid in an amount corresponding to the portion of excessive base is necessary. The reaction temperature is on the order of 20 to 100° C., preferably 40 to 80° C. The reaction time is preferably from 0.5 to 8 hours.

The solvent used in the acid hydrolysis reaction may be the same as the solvent for use in the halogenating step and dehydrohalogenation reaction or a mixed solvent obtained by addition of a different solvent, or the solvent may be replaced. In the case where no water is used in the halogenating step and the dehydrohalogenation reaction step, water at least equimolar or more with respect to the imine is necessary. Water may be added as a solvent in an amount range where the reaction compound will not precipitate from the reaction system.

In the present invention, the acid which can be used in acid hydrolysis includes organic and inorganic protic acids.

The organic acid which can be used includes carboxylic acids such as acetic acid, propionic acid, and trifluoroacetic acid, sulfonic acids such as methanesulfonic acid and p-toluenesulfonic acid, etc.

The inorganic acid which can be used includes sulfuric acid, hydrochloric acid, nitric acid, phosphoric acid, etc.

The solvent which can be used in the reaction in the present invention includes, for example, ethers such as dioxane and tetrahydrofuran, alcohols such as methanol, ethanol, propanol, and butanol, nitriles such as acetonitrile and propionitrile, halogenated hydrocarbons such as dichloromethane and 1,2-dichlorooethane, aprotic polar solvents such as dimethylformamide and dimethyl sulfoxide, etc. Also, water is used as a solvent. However, a reaction starting material, an intermediate or a product may sometimes precipitate and in order to prevent precipitation of a starting material, a product or the like, the above-mentioned organic solvents may be mixed. In this case, water and the organic solvent may be mixed to form a uniform system or when an organic solvent which is compatible with water is used, the reaction may be performed in a two-layer system. The same solvent may be used throughout the steps of halogenation, dehalogenation, and acid hydrolysis or the solvent is mixed or replaced depending on the solubility of each raw material, intermediate and product.

(b) A Process for Producing a Cyanobenzoyl Halide Compound

In the production process for cyanobenzoyl halide compound according to the present invention, the cyanobenzaldehyde compound which can be preferably used as a raw material is one that is obtained by the above-described process of the present invention. However, the present invention is not limited thereto. For example, unsubstituted cyanobenzaldehyde compound can be synthesized by oxidative deamination reaction such as Sommelet reaction of cyanobenzylamine obtained by reduction reaction of respective one of the two nitriles in the corresponding benzene-dinitrile (JP-A-49-85041).

Furthermore, of the halogenated cyanobenzaldehyde compound substituted with a halogen, chlorinated cyanobenzaldehyde compounds such as 3-cyano-2,4,5,6-tetrachlorobenzaldehyde and 4-cyano-2,3,5,6-tetrachlorobenzaldehyde can be synthesized by chlorinating isophthalonitrile or terephthalonitrile to synthesize tetrachloroisophthalonitrile or tetrachloroterephthalonitrile, then reducing one of nitrile groups of the tetrachloroisophthalonitrile or tetrachloroterephthalonitrile, and oxidatively deaminating the resultant 3-cyano-2,4,5,6-tetrachlorobenzylamine or 4-cyano-2,3,5,6-tetrachlorobenzylamine.

The fluorinated cyanobenzaldehyde compounds can be synthesized by reducing one of the nitrile groups in fluorinated phthalonitrile compound obtained by fluorination reaction of the above-described chlorinated phthalonitrile compound such as tetrachloroisophthalonitrile or tetrachloroterephthalonitrile to obtain cyanofluorobenzylamine compound such as 3-cyano-2,4,5,6-tetrafluorobenzylamine or 4-cyano-2,3,5,6-tetrafluorobenzylamine and subjecting them to oxidative deamination reaction.

In the production method for cyanobenzoyl halide compound according to the present invention, a halogenating agent is used in the acid halide formation of aldehyde groups.

Here, the halogenating agent is a generic name for reagents that introduce a halogen atom into the aldehyde group in the cyanobenzaldehyde compound to convert it to an acid halide group. Hereafter, the reaction is referred to as acid halide formation.

In the process of the present invention, the halogenating agents which can be used include halogen molecules such as chlorine and bromine, mixed halogen molecules such as bromine chloride (BrCl), haloimides or haloamides such as N-chlorosuccinimide, N-bromosuccinimide, and N-bromoacetoamide, hypohalogenous acid salts or hypohalogenous acid esters such as calcium hypochlorite $(Ca(ClO)_2)$ and t-butyl hypochlorite, chlorides or bromides such as sulfuryl chloride and sulfuryl bromide. However, the present invention is not limited thereto and halogenating agents that are used in organic syntheses in general may be used.

The amount of halogenating agent to be used is preferably 0.8 to 3 mol per mol of the cyanobenzaldehyde compound.

Furthermore, the reaction temperature is in the order of 50 to 150° C., preferably 40 to 100° C. The reaction time is preferably from 0.5 to 8 hours.

In the reaction between the cyanobenzaldehyde compound and the halogenating agent, a radical initiator may be used though not always necessary, to effectively promote the reaction.

The radical initiator includes azobis compounds such as azobisisobutyronitrile, diacyl peroxides such as benzoyl peroxide, dialkyl peroxides such as di-t-butyl peroxide and dicumyl peroxide, hydroperoxides such as t-butyl hydroperoxide and cumene hydroperoxide, alkyl peresters such as t-butyl peracetate and t-butyl perbenzoate, etc.

In the reaction in the present invention, the radical derived from halogen is released to promote the reaction according as the reaction proceeds, so that the amount of radical initiator to be added initially may be a catalytic amount.

In the process of the present invention, the reaction can be performed in a molten state by elevating the temperature of the cyanobenzaldehyde compound to its melting point without using any solvent. Furthermore, the corresponding cyanobenzoyl halide compound, reaction product, may be added to the cyanobenzaldehyde compound, raw material to decrease the melting point and perform the reaction at a lower temperature than that attained by using the cyanobenzaldehyde compound alone. The cyanobenzoyl halide compound to be added is used in a molar proportion of preferably 0.05 to 10 per cyanobenzaldehyde compound.

In the reaction in the present invention, a solvent may be used. The solvent may be any solvent so long as it decomposes neither the halogenating agent nor cyanobenzoyl halide compound and gives no adverse influence on the reaction. For example, there can be used halogenated hydrocarbons such as dichloromethane, chloroform, carbon tetrachloride, 1,2-dichloroethane, chlorobenzene, and dichlorobenzene, ethers such as 1,2-dimethoxyethane, dioxane, and diglyme, aromatic hydrocarbons such as benzene, nitrites such as acetonitrile and propionitrile, tertiary alcohols such as t-butanol, etc. These organic solvents may be used singly or two or more of them may be used as mixtures.

The amount of solvent to be used is preferably 1 to 50-folds based on the weight of the cyanobenzaldehyde compound.

(c) A Process for Producing Cyanobenzoic Acid Compound

The process for producing a cyanobenzoic acid compound according to the present invention can be performed by charging a cyanobenzaldehyde compound and a hypohalogenous compound, water or water and aprotic polar solvent as a solvent in a reaction vessel and allowing them to react with stirring at a predetermined temperature for a predetermined period of time.

The reaction starting materials may be charged and reacted at atmospheric pressure or under pressure, preferably at atmospheric pressure. The reaction vessel is suitably a glass vessel or an acid-proof metal vessel.

As the cyanobenzaldehyde compound used in the reaction of the present invention, those obtained by the above-mentioned production process of the present invention may be used advantageously. However, the present invention is not limited thereto and the unsubstituted cyanobenzaldehyde compounds, chlorinated cyanobenzaldehyde compounds, fluorinated cyanobenzaldehyde compounds, etc. synthesized by the method described in the column of the cyanobenzoyl halide (b) herein may also be used.

In the production method for the cyanobenzoic acid compounds of the present invention, a hypohalogenous acid compound is used in order to oxidize an aldehyde group.

In this reaction, the hypohalogenous compound may be used in a relatively broad pH range ranging from acidic, neutral to basic. If the pH of the reaction mixture is too low, decomposition that does not participate in the reaction of hypohalogenous compound is remarkable to increase the amount of hypohalogenous compound consumed until the reaction is completed while if the pH is too high, a side reaction, i.e., decomposition of nitrile groups in the cyanobenzaldehyde compound or the cyanobenzoic acid compound which is produced by the reaction tends to occur simultaneously, resulting in a decreased purity of cyanobenzoic acid compound. A pH in the range of from 5 to 10 is preferred. Upon the reaction, the hypohalogenous acid compound may be added in lump at the time of starting the reaction but it is preferred that it be added usually over from 5 minutes to 10 hours since otherwise there is the fear that the reaction could proceed abruptly to cause side reactions simultaneously.

The hypohalogenous compound which can be used in the production of cyanobenzoic acid compound includes hypohalogenous acids such as hypochlorous acid, hypobromous acid, and hypolodous acid, hypohalogenous acid salts such as sodium hypochlorite, potassium hypochlorite, calcium hypochlorite, barium hypochlorite, sodium hypobromide, potassium hypobromite, sodium hypoiodite, and potassium hypoiodite.

The amount of the hypohalogenous acid compound to be used in the reaction in the present invention is preferably in a molar proportion of from 1 to 5 per cyanobenzaldehyde compound.

In the production process of the present invention, a cyanobenzoic acid compound is produced and precipitates according as the cyanobenzaldehyde compound is oxidized. When the pH of the reaction mixture is approximately 4 or lower, there arise the problem that the cyanobenzoic acid compound precipitates abruptly in large amounts, so that stirring becomes difficult or the reaction is difficult to complete since unused cyanobenzaldehyde is incorporated in the cyanobenzoic acid compound which precipitated.

In such a case, addition of a base to the reaction system to convert the cyanobenzoic acid compound into the form of salt and have it dissolved in the reaction mixture to make the reaction system a uniform solution enables the reaction to proceed efficiently. The base may be added in a necessary amount in a lump initially or it may be added continually in accordance with the progress of the reaction so that the cyanobenzoic compound will not precipitate.

The base which can be used in the production of cyanobenzoic acid compounds according to the present invention includes hydroxides of alkali metals and alkaline earth metals, such as lithium hydroxide, sodium hydroxide, potassium hydroxide, magnesium hydroxide and calcium hydroxide, bicarbonates of alkali metals such as sodium hydrogen carbonate and potassium hydrogen carbonate, carbonates of alkali metals and alkaline earth metals, such as lithium carbonate, sodium carbonate, potassium carbonate, magnesium carbonate, and calcium carbonate, alkaline earth metal oxides, such as magnesium oxide and calcium oxide.

The amount of base to be used as described above may vary depending on the kind and amount of hypochlorous acid compound that coexists but is at least an equimolar amount as expressed as total amount of the base contained in the hypochlorous compound and the base to be added to the reaction with respect to the cyanobenzaldehyde compound and such an amount that the pH range of the reaction system during the reaction can be maintained in a pH range of from 5 to 10.

In the process of the present invention, the reaction may be performed in an aqueous solution. When water is used as a solvent and if the solubility of the cyanobenzaldehyde compound is low, the reaction can be performed efficiently by co-existence of an aprotic polar solvent.

The aprotic polar solvent which can be used in the reaction includes ethers such as dioxane and diglyme, amides such as dimethylformamide, sulfur-containing hydrocarbons such as dimethyl sulfoxide and sulfolane, and nitriles such as acetonitrile.

The amount of aprotic polar solvent used in the reaction in the present invention is at least 0.1 (part by weight) per unit (part by weight) of the cyanobenzaldehyde compound and in an amount where it is soluble in water, preferably, in an amount of 0.3 to 3 (parts by weight) of the aprotic polar solvent per unit (part by weight) of the cyanobenzaldehyde compound.

If the reaction temperature is too low, the reaction speed is low while if it is too high, nitrite groups tend to decompose, so that the reaction temperature is preferably form 10 to 80° C., more preferably from 30 to 50° C. The reaction time may vary depending on pH, composition of solvent, etc. but generally a time of from 10 minutes to 12 hours is preferred.

BEST MODE FOR CARRYING OUT THE INVENTION

Hereafter, the present invention will be described in more detail by examples. However, the present invention will not be limited thereto.

In Examples 1 to 24, Reference Example, and Examples 32 to 38, the high performance liquid chromatography was used for the analysis and determination under the following conditions:

Column: Shodex DE-513L+ Precolumn
Eluant: Water/acetonitrile/acetic acid=2250/750/15 (ml)
  Sodium 1-octanesulfonate: 6.45 g
Conditions: Flow rate; 1 ml/min, UV 254 nm
  Column oven: 40° C.

The gas chromatography used in the analyses of the cyanobenzoyl halide obtained in Examples 25 to 31 and 38 was run under the following conditions:

Column: CBP1-W12-300
Carrier: He flow rate 22.5 ml/min.
Analytical conditions:
  Initial Temperature: 100° C.
  Temperature elevation rate: 5° C./min
  Final temperature: 250° C.
  Splitless
Detection: FID

EXAMPLE 1

13.2 g of p-cyanobenzylamine was added dropwise to 200 ml of water and 15.8 g of potassium permanganate with vigorous stirring at room temperature over 20 minutes. The mixture was adjusted to pH 1 by sulfuric acid and stirred at room temperature for 5 hours. The p-cyanobenzaldehyde obtained had a yield of 26% (on a basis of cyanobenzylamine compound, hereafter the same) determined by the analysis of high performance liquid chromatography.

EXAMPLE 2

20 ml of wet-pyridine, 1.3 g of p-cyanobenzylamine, 0.5 g of sulfuric acid, and 0.1 g of cuprous chloride were mixed and while blowing air into the mixture was stirred at 100° C. for 15 hours. The obtained p-cyanobenzaldehyde had a yield of 12% by the analysis of high performance liquid chromatography.

EXAMPLE 3

20 ml of wet-pyridine, 1.3 g of p-cyanobenzylamine, 0.5 g of sulfuric acid, and 0.2 g of ruthenium chloride were mixed and while blowing air into the mixture was stirred at 100° C., for 20 hours. The obtained p-cyanobenzaldehyde had a yield of 8% by the analysis of high performance liquid chromatography.

EXAMPLE 4

20 ml of acetic acid, 1.3 g of p-cyanobenzylamine, and 0.3 g of sodium tungstate were mixed and 1.4 g of 30% by weight hydrogen peroxide was added thereto over 20 minutes and the mixture was allowed to react for additional 1 hour at the same temperature. The solution was sampled and after it was treated with sulfuric acid, it was analyzed by high performance liquid chromatography, showing that the obtained p-cyanobenzaldehyde had a yield of 11% or more.

EXAMPLE 5

13.2 g of p-cyanobenzylamine, 51 g of a 35% aqueous formalin solution and 24 g of a 28% aqueous ammonia solution were reacted at 90° C. for 2 hours while stirring in a solvent of which pH was adjusted to 3 by sulfuric acid. The reaction solution was cooled to room temperature and then cooled on ice for 2 hours. The crystals precipitated were collected by filtration, washed with water and dried to obtain 5.2 g (yield: 40%) of p-cyanobenzaldehyde. The p-cyanobenzaldehyde obtained had a purity of 99.5% or more determined by the analysis of high performance liquid chromatography.

EXAMPLE 6

39.6 g of p-cyanobenzylamine, 42.1 g of hexamethylenetetramine, 200 ml of water and 200 ml of acetic acid were mixed and reacted at 100° C. for 2 hours while stirring. The reaction solution was allowed to stand overnight and as a result, scale-like crystals were precipitated. The crystals precipitated were collected by filtration, washed with water and dried to obtain 24.7 g (yield: 62%) of p-cyanobenzaldehyde. The purity was 99.8% or more.

EXAMPLE 7

56.2 g of p-cyanobenzylamine, 59.6 g of hexamethylenetetramine, 46 ml of water, 320 ml of acetic acid and 46.0 g of 98% sulfuric acid were mixed and reacted at 100° C. for 2 hours while stirring. The reaction solution was concentrated to about a half amount in an evaporator and 400 ml of water was added to precipitate crystals. The crystals precipitated were collected by filtration, washed with water and dried to obtain 43.8 g (yield: 78%) of p-cyanobenzaldehyde. The purity was 99.8% or more.

EXAMPLE 8

39.6 g of p-cyanobenzylamine, 42.1 g of hexamethylenetetramine and 400 ml of water were mixed and after adjusting the pH of the solvent to 2.5 by sulfuric acid, the mixture was reacted at 90° C. for 2 hours while stirring. The reaction solution was cooled to room temperature and then cooled on ice. The crystals precipitated were collected by filtration, washed with water and dried to obtain 13.2 g (yield: 33%) of p-cyanobenzaldehyde. The purity was 99.8% or more.

EXAMPLE 9

39.6 g of p-cyanobenzylamine, 21.1 g of hexamethylenetetramine, 150 ml of water and 150 ml of acetic acid were mixed and reacted at 100° C. for 2 hours while stirring. The reaction solution was concentrated to a half amount in an evaporator and 300 ml of water was added to precipitate crystals. The crystals precipitated were collected by filtration, washed with water and dried to obtain 32.8 g (yield: 82%) of p-cyanobenzaldehyde. The purity was 99.5% or more.

EXAMPLE 10

7.9 g of p-cyanobenzylamine, 8.4 g of hexamethylenetetramine, 40 ml of water, 20 ml of acetic acid and 50 ml of toluene were mixed and reacted at 90° C. for 2 hours while stirring. The reaction solution was cooled to room temperature and the toluene layer was separated, washed with water and concentrated until crystals were precipitated. The concentrated toluene solvent was placed in water, the toluene was removed by azeotropic distillation, and the residue was cooled to room temperature. The crystals precipitated were collected by filtration, washed with water and dried to obtain 4.8 g (yield: 60%) of p-cyanobenzaldehyde. The purity was 99.5% or more.

EXAMPLE 11

3.9 g of p-cyanobenzylamine, 4.2 g of hexamethylenetetramine, 15 ml of methanol, 15 ml of water and 8 ml of acetic acid were mixed and after adjusting the pH of the solvent to 3 by sulfuric acid, the mixture was reacted at 70° C. for 5 hours while stirring. The reaction solution was concentrated to a half amount in an evaporator and 20 ml of water was added to precipitate crystals. The crystals precipitated were collected by filtration, washed with water and dried to obtain 1.8 g (yield: 45%) of p-cyanobenzaldehyde. The purity was 99.5% or more.

EXAMPLE 12

13.2 g of p-cyanobenzylamine, 12.0 g of paraformaldehyde, 46.0 g of ammonium acetate, 60 ml of water and 60 ml of acetic acid were mixed and reacted at 100° C. for 3 hours while stirring. The reaction solution was concentrated to a half amount in an evaporator and water in an amount equal to the amount of solvent distilled off was added to precipitate crystals. The crystals precipitated were collected by filtration, washed with water and dried to obtain 8.0 g (yield: 62%) of p-cyanobenzaldehyde. The purity was 99.5% or more.

EXAMPLE 13

13.2 g of p-cyanobenzylamine, 30.0 g of formaldehyde dimethyl acetal, 38.4 g of ammonium carbonate and 80 ml of water were reacted after adjusting the pH of the solvent to 2.5 by sulfuric acid, at 90° C. for 4 hours while stirring. The reaction solution was cooled to room temperature and then cooled on ice. The crystals precipitated were collected by filtration, washed with water and dried to obtain 5.1 g (yield: 39%) of p-cyanobenzaldehyde. The purity was 99.5% or more.

EXAMPLE 14

7.9 g of m-cyanobenzylamine, 8.4 g of hexamethylenetetramine, 40 ml of water and 40 ml of acetic acid were mixed and reacted at 104° C. for 2 hours while stirring. The reaction solution was cooled to room temperature and thereto 12 g of concentrated sulfuric acid was added. The solvent was concentrated to dry in an evaporator with a water bath at 70° C. The concentration residue was separated by toluene/water and washed with water. The toluene layer obtained was concentrated until crystals were precipitated. The concentrated toluene solvent was placed in water and after removing toluene by azeotropic distillation, the residue was cooled to room temperature. The crystals precipitated were collected by filtration, washed with water and dried to obtain 5.9 g (yield: 74%) of m-cyanobenzaldehyde. The purity was 99% or more.

EXAMPLE 15

13.2 g of m-cyanobenzylamine, 51 g of a 35% aqueous formalin solution, 24 g of a 28% aqueous ammonia solution and 50 ml of acetic acid were mixed and reacted at 100° C. for 3 hours while stirring. The reaction solution was concentrated to dry in an evaporator and thereto 100 ml of water was added to precipitate crystals. The crystals precipitated were collected by filtration, washed with water and dried to obtain 7 g (yield: 54%) of m-cyanobenzaldehyde. The purity was 99% or more.

EXAMPLE 16

600 g of m-cyanobenzylamine crude product (m-cyanobenzylamine 90% by weight, m-xylylenediamine 10% by weight) obtained by hydrogen reduction of isophthalonitrile in the presence of sponge metal nickel catalyst was added dropwise in 8 kg of water while stirring at room temperature for dissolution and the solution was left to stand overnight at 5C. The crystals which precipitated were filtered by centrifugation to obtain 783 g of m-cyanobenzylamine hydrate (water content: 48% by weight).

783 g of the m-cyanobenzylamine hydrate, 431 g of hexamethylenetetramine, 2.03 kg of acetic acid, and 300 g of 98% by weight sulfuric acid were mixed and allowed to react at 100° for 1 hour and 30 minutes. After cooling the reaction mixture to room temperature, 300 g of 98% by weight sulfuric acid was mixed therewith and the reaction mixture was concentrated to about a half amount in an evaporator and 3 liters of water was added to precipitate crystals.

Water in an amount equal to the amount of solvent distilled off was added to precipitate crystals. The crystals precipitated were collected by filtration, washed with water and dried to obtain 256 g (yield: 63%) of m-cyanobenzaldehyde. The purity was 99% or more.

EXAMPLE 17

194 kg of p-cyanobenzylamine crude product (p-cyanobenzylamine 92% by weight, p-xylylenediamine 8% by weight) obtained by hydrogen reduction of terephthalonitrile in the presence of sponge metal nickel catalyst was mixed with 1,100 kg of water while stirring at 40° C. or less and the mixture was stirred for 3 hours. The crystals which precipitated were separated by centrifugation while washing with water to obtain 197 kg of p-cyanobenzylamine hydrate (water content: 21% by weight).

197 g of the p-cyanobenzylamine hydrate, 164 kg of hexamethylenetetramine, and 775 kg of acetic acid were mixed and the internal temperature was elevated to 90° C. An aqueous sulfuric acid solution of 115 kg of 98% by weight sulfuric acid and 85 kg of water was added dropwise thereto over 20 minutes. Further, the reaction mixture was stirred at 1009 for 1 hour. After the internal temperature was decreased to 40° C., 115 kg of 98% by weight sulfuric acid was added. The reaction mixture was concentrated under reduced pressure to recover 698 kg of acetic acid solution. To the residue in the reaction vessel was added 950 kg of water to precipitate crystals. The precipitated crystals were collected by centrifugation while washing with water, and dried to obtain 110 kg (yield: 71%) of p-cyanobenzaldehyde. The purity was 99.5% or more.

EXAMPLE 18

168 kg of p-cyanobenzylamine crude product (p-cyanobenzylamine 92% by weight, p-xylylenediamine 8% by weight) obtained by hydrogen reduction of terephthalonitrile in the presence of sponge metal nickel catalyst was mixed with 680 kg of water while stirring at 40° C. or less and the mixture was stirred for 3 hours. The crystals which precipitated were separated by centrifugation while washing with water to obtain 155 kg of p-cyanobenzylamine hydrate (water content: 21% by weight).

171 g of the p-cyanobenzylamine hydrate, 143 kg of hexamethylenetetramine, and 672 kg of acetic acid were mixed and the internal temperature was elevated to 90° C. An aqueous sulfuric acid solution of 93 kg of 98% by weight sulfuric acid and 69 kg of water was added dropwise thereto over 20 minutes. Further, the reaction mixture was stirred at 100w for 1 hour. After the internal temperature was decreased to 40° C., 93 kg of 98% by weight sulfuric acid was added. The reaction mixture was concentrated under reduced pressure to recover 650 kg of acetic acid solution. To the residue in the reaction vessel was added 563 kg of water and 890 kg of toluene and stirred vigorously and thereafter left to stand. After removing the water layer, 250 kg of water was added, followed by vigorous stirring and left to stand to remove water (this operation being performed twice). The toluene was concentrated under reduced pressure to recover 570 kg of toluene. After reverting to atmospheric pressure, 290 kg of water was added and the mixture was concentrated until the distillation temperature reached 99° C. or more to recover 300 kg of toluene and 90 kg of water. The mixture was cooled to room temperature while stirring to precipitate crystals. The precipitated crystals were collected by centrifugation while washing with water, and dried to obtain 113 kg (yield: 84%) of p-cyanobenzaldehyde. The purity was 99.5% or more.

EXAMPLE 19

13.2 g of p-cyanobenzylamine, 28.6 g of sodium persulfate, 10 ml of water, and 100 ml of methanol were mixed and allowed to react at 50° C. for 40 minutes while stirring. After cooling the reaction mixture to room temperature, methanol was distilled off to precipitate solids. To the resulting suspension was added dichloromethane for extraction. The organic layer was washed twice with saturated aqueous sodium bicarbonate solution and then twice with water, and then magnesium sulfate was added thereto. The residue after distilling off dichloromethane was subjected to silica gel column chromatography (eluant: hexane/ethyl acetate=5/1), and hexane and ethyl acetate were distilled off. The resultant crude product concentrated to dryness was recrystallized from cyclohexane, the crystals were filtered, and dried to obtain 7.7 g (yield: 58%) of p-cyanobenzaldehyde. The obtained p-cyanobenzaldehyde had a purity of 99% by the analysis of high performance liquid chromatography.

EXAMPLE 20

13.2 g of m-cyanobenzylamine, 23.8 g of sodium persulfate and 200 ml of water were mixed and allowed to react at 70° C. for 2 hours while stirring. After cooling the reaction mixture to room temperature, sodium bicarbonate was added to render the solution weakly alkaline. The solution was subjected to separation, column chromatography, and crystallization operations in the same manner as in Example 19 to obtain 6.7 g (yield: 51%) of m-cyanobenzaldehyde. The purity was 98%.

EXAMPLE 21

13.2 g of m-cyanobenzylamine, 23.8 g of sodium persulfate and 200 ml of water were mixed and the mixture was reacted with 0.2 g of silver nitrate at 40° C. for 2 hours while stirring. The obtained m-cyanobenzaldehyde had a yield of 68% by the analysis of high performance liquid chromatography.

Reference Example: Dimerization of p-cyanobenzylimine 2.0 g of p-cyanobenzylimine, 4.3 g of sodium persulfate, 3.0 g of sodium hydrogen carbonate, 40 ml of water were mixed and allowed to react at 50° C. for 4 hours while stirring. The solids which precipitated were collected by filtration, washed with water and dried to obtain 1.7 g (yield: 92%) of p-cyanobenzylamine dimer. The HPLC area percentage was 95%.

EXAMPLE 22

13.2 g of p-cyanobenzylamine and 300 ml of t-butyl alcohol were mixed and 11.9 g of t-butyl hypochlorite was added dropwise at 50° C. over 30 minutes while stirring. After cooling the mixture to room temperature, 12.3 g of potassium t-butoxide was added and stirred at 60° C. for 3 hours. After cooling the reaction mixture to room temperature, 60 g of 10% by weight sulfuric acid was added dropwise over 1 hour and the mixture was stirred for additional 1 hour. The reaction mixture was adjusted to pH 6 by addition of sodium acetate and the solvent was distilled off under reduced pressure. The residue was extracted with toluene and the toluene layer was washed with water. After distilling off the toluene, evaporation under reduced pressure (135° C./15 mmHg) afforded 7.3 g (yield: 56%) of p-cyanobenzaldehyde. The obtained p-cyanobenzaldehyde had a purity of 98% by the analysis of high performance liquid chromatography.

EXAMPLE 23

6.6 g of m-cyanobenzylamine, 10.7 g of N-bromosuccinimide, 0.1 g of azobisisobutyronitrile, and 100 ml of 1,2-dichloroethane were mixed and allowed to react at 70° C. for 2 hours while stirring. After cooling the mixture to room temperature, 6.4 g of sodium carbonate and 40 ml of water were added and stirred vigorously for 2 hours. 50 ml of acetic acid was added and the mixture was stirred vigorously at 60° C. for 3 hours. Then, the solvent was distilled off under reduced pressure and water and toluene were added to the residue and the mixture was stirred. The insoluble components were filtered and the toluene layer was collected. After distilling off the toluene, the obtained crude product was recrystallized from cyclohexane to obtain 3.4 g (yield: 52%). The obtained m-cyanobenzaldehyde had a purity of 97% by the analysis of high performance liquid chromatography.

EXAMPLE 24

13.2 g of p-cyanobenzylamine and 200 ml of acetic acid were mixed and 160 g of an aqueous sodium hypochlorite solution (concentration: 14% by weight) was added dropwise at 50° C. over 30 minutes while stirring. The mixture was stirred for additional 1 hour at the same temperature. The obtained p-cyanobenzaldehyde had a yield of 43% by the analysis of high performance liquid chromatography.

EXAMPLE 25

52.2 g of p-cyanobenzaldehyde and 2.0 g of 2,2-azobisisobutyronitrile were mixed and 41.5 g of chlorine was bubbled over 2 hours and 30 minutes while stirring vigorously at 110° C. After introducing dry nitrogen gas into the reaction mixture for 1 hour, the reaction mixture was distilled under reduced pressure to obtain 54.7 g (yield on a basis of p-cyanobenzaldehyde: 83%) of p-cyanobenzoyl chloride (boiling point: 110° C./2 mmHg). The obtained p-cyanobenzoyl chloride had a purity of 99% or more by the analysis of gas chromatography.

EXAMPLE 26

26.2 g of p-cyanobenzaldehyde, 2.0 g of 2,2-azobisisobutyronitrile, and 50 ml of chlorobenzene were mixed and 36.0 g of chlorine was bubbled over 2 hours while stirring vigorously at 80° C. Dry nitrogen gas was introduced into the reaction mixture for 1 hour. The obtained p-cyanobenzoyl chloride had a yield of 91% (on a basis of p-cyanobenzaldehyde) by the analysis of gas chromatography.

EXAMPLE 27

26.2 g of p-cyanobenzaldehyde, 33.1 g of p-cyanobenzoyl chloride, and 2.0 g of 2,2-azobisisobutyronitrile, were mixed and 36.0 g of chlorine was bubbled over 2 hours while stirring vigorously at 80° C. Dry nitrogen gas was introduced into the reaction mixture for 1 hour. The obtained p-cyanobenzoyl chloride had a yield of 93% (on a basis of p-cyanobenzaldehyde) by the analysis of gas chromatography.

EXAMPLE 28

13.1 g of m-cyanobenzaldehyde, 16.5 g of m-cyanobenzoyl chloride, and 1.0 g of 2,2-azobisisobutyronitrile, were mixed and 18.0 g of chlorine was bubbled over 1 hour while stirring vigorously at 80° C. Dry nitrogen gas was introduced into the reaction mixture for 1 hour. The obtained m-cyanobenzoyl chloride had a yield of 90% (on a basis of m-cyanobenzaldehyde) by the analysis of gas chromatography.

EXAMPLE 29

13.1 g of p-cyanobenzaldehyde, 0.5 g of 2,2-azobisisobutyronitrile, and 120 ml of t-butanol were mixed and 21.6 g of t-butyl hypochlorite was added over 1 hour while stirring vigorously at 80° C., and the mixture was stirred for additional 2 hours. Dry nitrogen gas was introduced into the reaction mixture for 1 hour. Then, the solvent was distilled under reduced pressure to obtain 14.2 g (86% on a basis of p-cyanobenzaldehyde) (boiling point: 110° C./2 mmHg). The obtained p-cyanobenzoyl chloride had a purity of 99% or more by the analysis of gas chromatography.

EXAMPLE 30

13.1 g of m-cyanobenzaldehyde, 0.5 g of 2,2-azobisisobutyronitrile, 24.0 g of N-chlorosuccinimide, and 150 ml of chlorobenzene were mixed and stirred at 90° C. for 5 hours vigorously. The obtained m-cyanobenzoyl chloride had a yield of 88% (on a basis of m-cyanobenzaldehyde)by the analysis of gas chromatography.

EXAMPLE 31

13.1 g of p-cyanobenzaldehyde, 0.5 g of 2,2-azobisisobutyronitrlle, 26.7 g of N-bromosuccinimide, and 150 ml of chlorobenzene were mixed and stirred at 90 for 4 hours vigorously. A portion of the reaction mixture was sampled, to which was added water/sodium carbonate and the mixture was analyzed by high performance liquid chromatography as p-cyanobenzoic acid. As a result, the obtained p-cyanobenzoyl bromide had a yield of 82% (on a basis of p-cyanobenzaldehyde).

EXAMPLE 32

While mixing 13.1 g of p-cyanobenzaldehyde and 50 g of water with stirring, 150 g of an aqueous 13% by weight sodium hypochlorite solution was added dropwise over 2 hours and subsequently the mixture was stirred for additional 1 hour. Then, 3 g of urea was added and the mixture was stirred for 20 minutes and further 8 g of 98% by weight sulfuric acid and 150 g of water were added.

The precipitated crystals were filtered, washed with water, and dried to obtain 12.1 g (yield: 82%) of p-cyanobenzoic acid. The obtained p-cyanobenzoic acid had a purity of 95% or more by the analysis of high performance liquid chromatography.

EXAMPLE 33

While mixing 26.2 g of p-cyanobenzaldehyde, 26 g of acetonitrile, 10.5 g of sodium carbonate, and 100 g of water with stirring, 210 g of an aqueous 13.5% by weight sodium hypochlorite solution was added dropwise over 1 hour while maintaining the internal temperature of the reaction system at 50° C. or less, and the resulting mixture was stirred for additional 1 hour. Then, 3.6 g of urea was added and the resulting mixture was stirred for 20 minutes. Furthermore, 12 g of 98% by weight sulfuric acid and 300 g of water were added.

The precipitated crystals were filtered, washed with water, and dried to obtain 27.6 g (yield: 94%) of p-cyanobenzoic acid. The purity was 98% or more.

EXAMPLE 34

26.2 g of p-cyanobenzaldehyde, 26 g of acetonitrile, 17.6 g of sodium hydrogen carbonate, and 100 g of water were mixed with stirring. 210 g of an aqueous 13.5% by weight sodium hypochlorite solution adjusted to a pH of 9 was added dropwise over 1 hour while maintaining the internal temperature of the reaction system at 50° C. or less, and the resulting mixture was stirred for additional 1 hour. Then, 3.6 g of urea was added and the resulting mixture was stirred for 20 minutes. Furthermore, 12 g of 98% by weight sulfuric acid and 300 g of water were added.

The precipitated crystals were filtered, washed with water, and dried to obtain 28.8 g (yield: 98%) of p-cyanobenzoic acid. The purity was 99% or more.

EXAMPLE 35

26.2 g of m-cyanobenzaldehyde, 40 g of dioxane, 17.6 g of sodium hydrogen carbonate, and 100 g of water were mixed with stirring. 210 g of an aqueous 13.5% by weight sodium hypochlorite solution adjusted to a pH of 9 was added dropwise over 1 hour while maintaining the internal temperature of the reaction system at 50° C. or less, and the resulting mixture was stirred for additional 1 hour. Then, 3.6 g of urea was added and the resulting mixture was stirred for 20 minutes. Furthermore, 12 g of 98% by weight sulfuric acid and 300 g of water were added.

The precipitated crystals were filtered, washed with water, and dried to obtain 27 g (yield: 92%) of m-cyanobenzoic acid. The purity was 98% or more.

EXAMPLE 36

26.2 g of m-cyanobenzaldehyde, 18 g of dimethylformamide, and 70 g of water were mixed with stirring. 220 g of an aqueous 13% by weight sodium hypochlorite solution was added dropwise over 2 hour while maintaining the internal temperature of the reaction system at 35 to 45° C. or less, and at the same time an aqueous sodium hydroxide solution was added dropwise using a drop funnel equipped with a pH controller so that the pH of the reaction mixture was 7 to 8. Then, 3.6 g of urea was added and the resulting mixture was stirred for 20 minutes. Furthermore, 12 g of 98% by weight sulfuric acid and 300 g of water were added.

The precipitated crystals were filtered, washed with water, and dried to obtain 26.5 g (yield: 90%) of m-cyanobenzoic acid. The purity was 98% or more.

EXAMPLE 37

20 kg of p-cyanobenzylamine crude product (p-cyanobenzylamine 92% by weight, p-xylylenediamine 8% by weight) obtained by hydrogen reduction of terephthalonitrile in the presence of sponge metal nickel catalyst was mixed with 90 kg of water while stirring at 40° C. or less and the mixture was stirred for 3 hours. The crystals which precipitated were separated by centrifugation while washing with water to obtain 20 kg of p-cyanobenzylamine hydrate (water content: 22% by weight). 20 kg of the p-cyanobenzylamine hydrate, 17.6 kg of hexamethylenetetramine, and 83 kg of acetic acid were mixed and the internal temperature was elevated to 80° C. while stirring. An aqueous sulfuric acid solution of 12.6 kg of 98% by weight sulfuric acid and 9.3kg of water was added dropwise thereto over 20 minutes. Further, the reaction mixture was stirred at 100° C. for 1 hour. After the internal temperature was decreased to 50° C., 12.6 kg of 98% by weight sulfuric acid was added. The reaction mixture was concentrated under reduced pressure to recover 75 kg of acetic acid solution. Totheresidue inthereaction vesselwas added 60 kg of water and 70 kg of toluene and stirred vigorously and thereafter left to stand. After removing the water layer, 20 kg of water was added, followed by vigorous stirring and left to stand to remove water (this operation being performed twice). The toluene was concentrated under reduced pressure to recover 48 kg of toluene. After reverting to atmospheric pressure, 54 kg of water was added and the mixture was concentrated until the distillation temperature reached a constant value (distillation of toluene was completed) to recover 21 kg of toluene and 6 kg of water. The mixture was cooled to room temperature while stirring (the mixture became an aqueous solution from which p-cyanobenzaldehyde had precipitated). 12.0 kg of acetonitrile and 8.0 kg of sodium hydrogen carbonate were mixed therewith and 125 kg of an aqueous 13.5% by weight sodium hypochlorite solution was added dropwise over 2 hours while maintaining the internal temperature of the reaction system at around 40° C. (±5° C.), and the mixture was stirred for additional 1 hour. Then, 2.1 kg of urea was added and stirred for 20 minutes and further 7.5 kg of 98% by weight sulfuric acid and 190 kg of water were added. The precipitated crystals were collected by centrifugation while washing with water, and dried to obtain 16.5 kg (yield: 94%) of p-cyanobenzoic acid. The purity was 99% or more.

EXAMPLE 38

500 g of p-cyanobenzylamine crude product (p-cyanobenzylamine 92% by weight, p-xylylenediamine 8% by weight) obtained by hydrogen reduction of terephthalonitrile in the presence of sponge metal nickel catalyst was mixed with 2.5 kg of water while stirring at 40° C. or less and the mixture was stirred for 3 hours. The crystals which precipitated were separated by centrifugation while washing with water to obtain 500 g of p-cyanobenzylamine hydrate (water content: 21% by weight). 500 g of the p-cyanobenzylamine hydrate, 420 g of hexamethylenetetramine, and 2.0 kg of acetic acid were mixed and the internal temperature was elevated to 80° C. while stirring. An aqueous sulfuric acid solution of 300 g of 98% by weight sulfuric acid and 165 g of water was added dropwise thereto over 20 minutes. Further, the reaction mixture was stirred at 100° C. for 1 hour. After the internal temperature was decreased to 50° C., 300 g of 98% by weight sulfuric acid was added. The reaction mixture was concentrated to dryness under reduced pressure. To the concentrated residue was added 900 g of 1% by weight sulfuric acid and stirred vigorously at 100° C. for 3 hours. Thereafter, the reaction mixture was cooled to room temperature for 2 hours. The crystals which precipitated were filtered, washed with water, and dried to obtain 295 g (yield: 75%) of p-cyanobenzaldehyde. The purity was 99.5% or more. Under nitrogen atmosphere, 295 g of the p-cyanobenzaldehyde and 4.5 g of 2,2-azobisisobutyronitrile were mixed. The temperature was elevated to 105° C. and 190 g of chlorine was bubbled over 3 hours with vigorous stirring. After dry nitrogen gas was introduced into the reaction mixture for 1 hour, the solvent was distilled under reduced pressure to obtain 302 g (yield: 81%) of p-cyanobenzoyl chloride. The purity was 98.5%.

INDUSTRIAL APPLICABILITY

According to the present invention, cyanobenzaldehyde compounds can be produced in an improved yield and in an improved purity by oxidation using an oxidizing agent of cyanobenzylamine compound that is readily obtained from a phthalonitrile compound.

Furthermore, according to the present invention, cyanobenzoyl halide compounds can be produced in a high purity and in a high yield on an industrial scale starting from the cyanobenzaldehyde compound that can be obtained in large amounts at low costs by the above-described method under simplified and convenient reaction conditions with reducing loads on the environment to a greater extent than the conventional methods.

Furthermore, according to the present invention, cyanobenzoic acid compounds can be produced in a high purity and in a high yield under simplified and convenient reaction conditions using cyanobenzaldehyde compounds that are readily available in large amounts and inexpensively without using compounds having the possibility of generating hydrogen cyanide or the like. Upon the reaction, the wastes are safe and clean and there is by-produced no heavy metal-containing substance that pollutes the environment.

The cyanobenzaldehyde compounds, cyanobenzoyl halide compounds and cyanobenzoic acid compounds obtained by the process of the present invention are important intermediates for medical preparations, agricultural chemicals, liquid crystals, functional high molecular monomers and the like.

What is claimed is:

1. A process for producing a cyanobenzaldehyde compound comprising reacting a cyanobenzylamine compound with an oxidizing agent.

2. The proces's for producing a cyanobenzaldehyde compound as claimed in claim 1, wherein the cyanobenzylamine compound is obtained by reducing a phthalonitrile compound with hydrogen is reacted with the oxidizing agent.

3. The process for producing a cyanobenzaldehyde compound as claimed in claim 1, wherein the reaction with the oxidizing agent is performed in the presence of a transition metal compound.

4. The process for producing a cyanobenzaldehyde compound as claimed in claim 3, wherein the reaction with the oxidizing agent is performed in the presence of a transition metal compound with at least a second oxidizing agent different from the transition metal compound.

5. The process for producing a cyanobenzaldehyde compound as claimed in claim 4, wherein the second oxidizing agent is air.

6. The process for producing a cyanobenzaldehyde compound as claimed in claim 1, wherein the reaction with the oxidizing agent is performed in the presence of ammonia and formaldehyde or a condensate thereof and water under acidic conditions.

7. The process for producing a cyanobenzaldehyde compound as claimed in claim 1, wherein the reaction with the oxidizing agent is performed in a mixed solvent of water and an organic solvent.

8. The process for producing a cyanobenzaldehyde compound as claimed in claim 1, wherein the reaction with the oxidizing agent is performed in a solvent at a pH in the range of from 1.5 to 6.5.

9. The process for producing a cyanobenzaldehyde compound as claimed in claim 6, wherein the condensate between ammonia and formaldehyde is hexamethylenetetramine.

10. The process for producing a cyanobenzaldehyde compound as claimed in claim 1, wherein the oxidizing agent is a persulfate salt and the reaction is performed in an aqueous solution.

11. The process for producing a cyanobenzaldehyde compound as claimed in claim 10, wherein the reaction with the oxidizing agent is perf ormed in an aqueous solution further containing an organic solvent.

12. The process for producing a cyanobenzaldehyde compound as claimed in claim 1, wherein the reaction with the oxidizing agent is performed by reacting a cyanobenzylamine compound with a halogenating agent, and then with a basic compound, and further treating the reaction product with an acidic aqueous solution.

13. The process for producing a cyanobenzaldehyde compound as claimed in claim 12, wherein the reaction with the oxidizing agent is performed in the presence of a radical initiator.

14. The process for producing a cyanobenzaldehyde compound as claimed in claim 13, wherein the cyanobenzylamine compound is a compound represented by the following general formula (I):

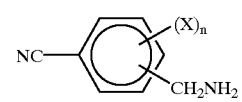

(I)

wherein —$CH_2NH_2$ and —X represent substituents on the benzene ring, —$CH_2NH_2$ is present at the meta- or para-position of the cyano group, and X represents a chlorine atom or a fluorine atom, and n is 0 or an integer of 1 to 4, provided that when n is 2 or greater, X groups may be the same or different, and the cyanobenzaldehyde compound is a compound represented by the following general formula (II)

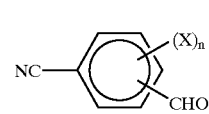

(II)

wherein —CHO and —X represent substituents on the benzene ring, —CHO is present at the meta- or para-position of the cyano group, X represents a chlorine atom or a fluorine atom, n represents 0 or an integer of from 1 to 4, provided that when n is 2 or greater, the X groups may be the same or different.

15. The process for producing a cyanobenzaldehyde compound as claimed in claim 14, wherein the cyanobenzylamine compound represented by the general formula (I) is p- or m-cyanobenzylamine and the cyanobenzaldehyde compound represented by the general formula (II) is corresponding p- or m-cyanobenzaldehyde.

16. A process for producing a cyanobenzoyl halide compound, comprising reacting cyanobenzylamine compound with the oxidizing agent to form a cyanobenzaldehyde compound and then converting an aldehyde group into an acid halide group without impairing the cyano group on the benzene ring of the cyanobenzaldehyde compound.

17. The process for producing a cyanobenzoyl halide compound as claimed in claim 16, wherein the aldehyde group is converted into the acid halide group with a halogenating agent.

18. The process for producing a cyanobenzoyl halide compound as claimed in claim 17, wherein the reaction is performed in the presence of a radical initiator.

19. The process for producing a cyanobenzoyl halide compound as claimed in claim 17, wherein the halogenating agent is chlorine and the acid halide group is an acid chloride.

20. The process for producing a cyanobenzoyl halide compound as claimed in claim 16, further comprising converting an aldehyde group in a cyanobenzaldehyde compound into an acid halide group is performed in a molten state by mixing the cyanobenzaldehyde with a reaction product.

21. The process for producing a cyanobenzoyl halide compound as claimed in claim 16, wherein the cyanobenzaldehyde compound is a compound represented by the following general formula (II)

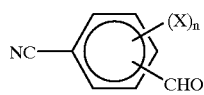

(II)

wherein —CHO and —X represent substituents on the benzene ring, —CHO is present at the meta- or para-position of the cyano group, X represents a chlorine atom or a fluorine atom, n represents 0 or an integer of from 1 to 4, provided that when n is 2 or greater, the X groups may be the same or different, and the cyanobenzoyl halide compound is a compound represented by the following general formula (IV)

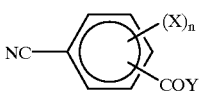

(IV)

wherein —COY and —X represent substituents on the benzene ring, —COY is present at the meta- or para-position of the —CN, X represents a chlorine atom or a fluorine atom, and n represents 0 or an integer of from 1 to 4 and Y represents a chlorine atom or a fluorine atom, provided that when n is 2 or greater, the X groups may be the same or different.

22. The process for producing a cyanobenzoyl halide compound as claimed in claim 21, wherein the cyanobenzaldehyde represented by the general formula (II) is m-cyanobenzaldehyde or p-cyanobenzaldehyde and the cyanobenzoyl halide compound represented by the general formula (IV) is m-cyanobenzoyl chloride or p-cyanobenzoyl chloride correspondingly.

23. A process for producing a cyanobenzoic acid compound, comprising reacting a cyanobenzylamine compound with an oxidizing agent to form a cyanobenzaldehyde compound and then oxidizing the aldehyde group without impairing the cyano group on the benzene ring of the cyanobenzaldehyde compound.

24. A process for producing a cyanobenzoic acid compound represented by the general formula (V)

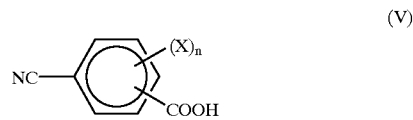

(V)

wherein —COOH and —X represent substituents on the benzene ring, —COOH is present at the meta- or para-position of the —CN, X represents a chlorine atom or a fluorine atom, n represents 0 or an integer of from 1 to 4, provided that when n is 2 or greater, the X groups may be the same or different, comprising reacting a cyanobenzaldehyde compound represented by the general formula (II)

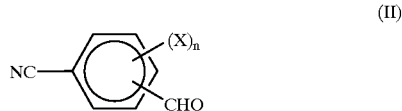

(II)

wherein —CHO and —X represent substituents on the benzene ring, —CHO is present at the meta- or para-position of the —CN, X represents a chlorine atom or a fluorine atom, n represents 0 or an integer of from 1 to 4, provided that when n is 2 or greater, the X groups may be the same or different, with a hypohalogenous acid compound.

25. The process for producing a cyanobenzoic acid compound as claimed in claim 24, wherein the reaction of the cyanobenzaldehyde compound with the hypohalogenous compound is performed in an aqueous solution in the presence of aprotic polar solvent.

26. The process for producing a cyanobenzoic acid compound as claimed in claim 24, wherein the reaction of the cyanobenzaldehyde compound with the hypohalogenous compound is performed in an aqueous solution at a pH in the range of from 5 to 10.

27. The process for producing a cyanobenzoic acid compound as claimed in claim 24, wherein the cyanobenzaldehyde represented by the general formula (II) is m-cyanobenzaldehyde or p-cyanobenzaldehyde and the cyanobenzoic acid compound represented by the general formula (V) is m-cyanobenzoic acid or p-cyanobenzoic acid respectively.

* * * * *